United States Patent
O'Hara Lauchle et al.

(10) Patent No.: US 11,918,561 B2
(45) Date of Patent: Mar. 5, 2024

(54) TREATMENT OF BREAST CANCER USING COMBINATION THERAPIES COMPRISING GDC-9545 AND A CDK4/6 INHIBITOR

(71) Applicant: Genentech, Inc., South San Francisco, CA (US)

(72) Inventors: Jennifer O'Hara Lauchle, Larkspur, CA (US); Sandra Milan, Orinda, CA (US); Melanie Carol Smitt, Portola Valley, CA (US); Marjorie C. Green, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 165 days.

(21) Appl. No.: 17/316,455

(22) Filed: May 10, 2021

(65) Prior Publication Data

US 2021/0353601 A1 Nov. 18, 2021

Related U.S. Application Data

(60) Provisional application No. 63/023,501, filed on May 12, 2020.

(51) Int. Cl.
| | |
|---|---|
| A61P 35/00 | (2006.01) |
| A61K 31/437 | (2006.01) |
| A61K 31/519 | (2006.01) |
| A61K 38/09 | (2006.01) |

(52) U.S. Cl.
CPC .......... *A61K 31/437* (2013.01); *A61K 31/519* (2013.01); *A61K 38/09* (2013.01); *A61P 35/00* (2018.01)

(58) Field of Classification Search
CPC .............................. A61P 35/00; A61K 31/437
See application file for complete search history.

(56) References Cited

U.S. PATENT DOCUMENTS

| | | |
|---|---|---|
| 9,980,947 B2 | 5/2018 | Labadie et al. |
| 10,954,234 B2 | 3/2021 | Chung et al. |
| 11,081,236 B2 | 8/2021 | Daemen et al. |

FOREIGN PATENT DOCUMENTS

| | | |
|---|---|---|
| JP | 2018-518529 A | 7/2018 |
| JP | 2019-508428 A | 3/2019 |
| WO | 2016/176666 A1 | 11/2016 |
| WO | 2017/160990 A1 | 9/2017 |

OTHER PUBLICATIONS

International Search Report and Written Opinion for PCT/US2021/031491 dated Aug. 10, 2021.
Metcalfe et al., "Abstract P5-04-07: GDC-9545: A novel ER antagonist and clinical candidate that combines desirable mechanistic and pre-clinical DMPK attributes" Cancer Res. (Published Feb. 2019 ( retrieved on Aug. 12, 2021), 79(4):Abstract P5-04-07.
Daemen et al., "Abstract P2-11-05: ER pathway activity signature as a biomarker for endocrine agent GDC-9545" Cancer Res 80(4 Supplement):P2-11-05 (Feb. 15, 2020).
Jhaveri, K., et al., "A first-in-human phase I study to evaluate the oral selective estrogen receptor degrader (SERD), GDC-9545, in postmenopausal women with estrogen receptor-positive (ER+) HER2-negative (HER2-) metastatic breast cancer" Poster (Abstract PD7-05; Cancer Res 80:Suppl. 4(Feb. 15, 2020)) San Antonio Breast Cancer Symposium [SABCS], San Antonio, Texas—US, pp. 1-4 ( Dec. 10-14, 2019).

*Primary Examiner* — Bruck Kifle
(74) *Attorney, Agent, or Firm* — Kevin M. Clark (57) ABSTRACT

Provided herein are combination therapies comprising GDC-9545 and a CDK4/6 inhibitor for treating locally advanced breast cancer or metastatic breast cancer.

27 Claims, 2 Drawing Sheets

FIG. 2

TREATMENT OF BREAST CANCER USING COMBINATION THERAPIES COMPRISING GDC-9545 AND A CDK4/6 INHIBITOR

CROSS REFERENCE TO RELATED APPLICATIONS

This Application claims the benefit of U.S. Provisional Patent Application No. 63/023,501, filed 12 May 2020, which is incorporated herein by reference in its entirety and for all purposes.

FIELD OF THE INVENTION

Provided herein are combination therapies comprising GDC-9545 or a pharmaceutically acceptable salt thereof and a CDK4/6 inhibitor (e.g. palbociclib) for the treatment of breast cancers.

BACKGROUND

Despite the effectiveness of endocrine therapies for ER-positive (ER+) breast cancer, many patients ultimately relapse or develop resistance. One such resistance mechanism involves mutations in ESR1 that drive ER-dependent transcription and proliferation in the absence of estrogen.

Accordingly, there is a pressing need for clinically active agents for treatment of relapsed or resistant ER-positive breast cancer.

SUMMARY

Provided herein are solutions to the problems above and other problems in the art.

The present embodiments can be understood more fully by reference to the detailed description and examples, which are intended to exemplify non-limiting embodiments.

DETAILED DESCRIPTION

Figure 1:
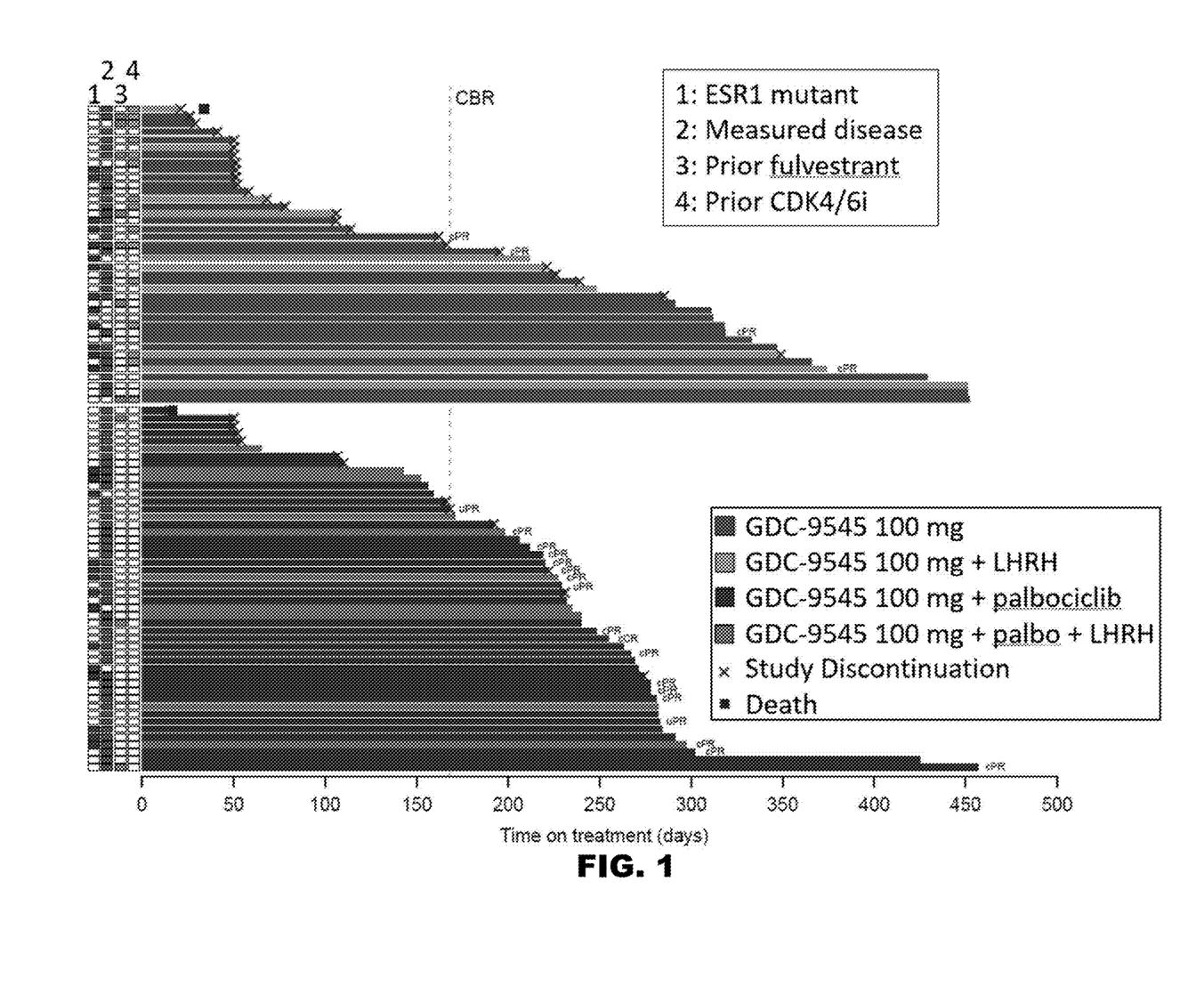
FIG. 1 depicts a plot of time on study for patients described herein treated with combination therapy of GDC-9545 and palbociclib. uPR=unconfirmed partial response; cPR=confirmed partial response.
Figure 2:
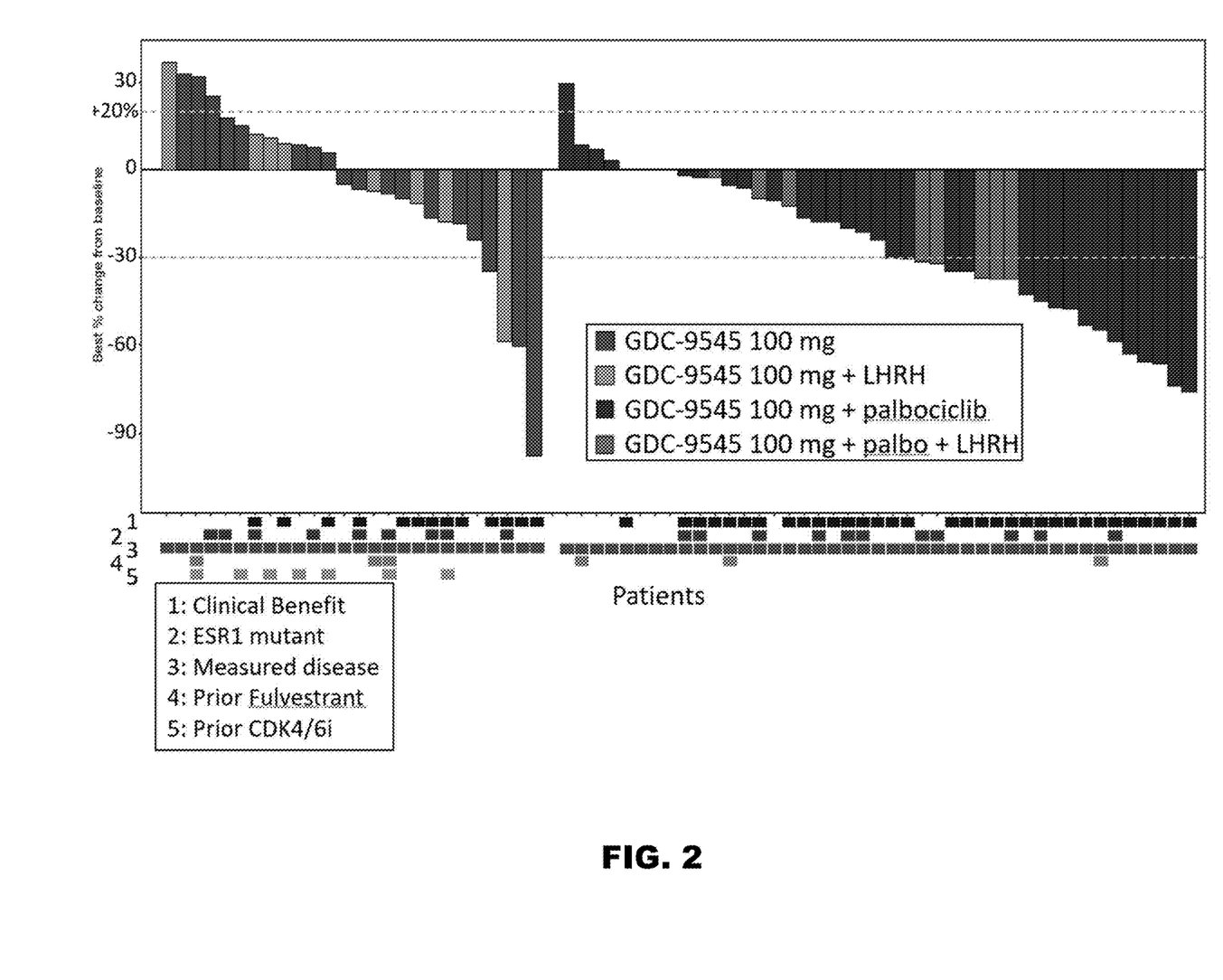
FIG. 2 depicts the tumor response across patients treated with GDC-9545 and GDC-9545 and palbociclib.

Unless defined otherwise, all technical and scientific terms used herein have the same meaning as commonly understood by those of ordinary skill in the art to which the invention belongs. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention.

The following definitions are provided to facilitate understanding of certain terms used frequently herein and are not meant to limit the scope of the present disclosure. All references referred to herein are incorporated by reference in their entirety.

As used herein, and unless otherwise specified, the terms "about" and "approximately," when referring to doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. The equivalent dose, amount, or weight percent can be within 30%, 20%, 15%, 10%, 5%, 1%, or less of the specified dose, amount, or weight percent.

"GDC-9545" refers to a compound having the structure:

having the chemical name 3-((1R,3R)-1-(2,6-difluoro-4-((1-(3-fluoropropyl)azetidin-3-yl)amino)phenyl)-3-methyl-1,3,4,9-tetrahydro-2H-pyrido[3,4-b]indol-2-yl)-2,2-difluoropropan-1-ol. GDC-9545 is also known as giredestrant. In one embodiment, GDC-9545 is a tartrate salt.

"Palbociclib" refers to a compound having the structure:

having the chemical name 6-acetyl-8-cyclopentyl-5-methyl-2-{[5-(piperazin-1-yl)pyridin-2-yl]amino}pyrido[2,3-d]pyrimidin-7(8H)-one. Palbociclib is marketed under the tradename IBRANCE®. Palbociclib is an exemplary "CDK4/6 inhibitor"—a class of agents targeting cyclin dependent kinase 4 and 6 (CDK4 and CDK6, respectively).

Other exemplary CDK4/6 inhibitors include, but are not limited to: ribociclib (Butanedioic acid-7-cyclopentyl-N,N-dimethyl-2-{[5-(piperazin-1-yl) pyridin-2-yl]amino}-7H-pyrrolo[2,3-d]pyrimidine-6-carboxamide (1/1); marketed as KISQALI®); abemaciclib, (2-Pyrimidinamine, N-[5-[(4-ethyl-1-piperazinyl)methyl]-2-pyridinyl]-5-fluoro-4-[4-fluoro-2-methyl-1-(1-methylethyl)-1H-benzimidazol-6-yl], marketed as VERZENIO®); and Trilaciclib (2'-((5-(4-methylpiperazin-1-yl)pyridin-2-yl)amino)-7',8'-dihydro-6'H-spiro(cyclohexane-1,9'-pyrazino(1',2':1,5)pyrrolo(2,3-d)pyrimidin)-6'-one).

"Time to deterioration in pain level" refers to the time to the first documented increase by at least 2 points from a baseline measurement (e.g. by using the Brief Pain Inventory-Short Form (BPI-SF) questionnaire).

"Time to deteriortation in pain presence and inference" refers to the time to the first documented increase by at least 10 points from a baseline measurement (e.g. by using the European Organization for Research and Treatment of Cancer Quality-of-Life Questionnaire (EORTC QLQ-C30) Linearly Transformed Pain Scale).

"Time to Deterioration in Physical Functioning" refers to time to the first documented decrease by at least 10 points from a baseline measurement (e.g. by using the in the EORTC QLQ-C30 Linearly Transformed Physical Functioning Scale Score).

"Time to Deterioration in Role Functioning" refers to the time to the first documented decrease of at least 10 points from a baseline measurement (e.g. by using the the EORTC QLQ-C30 Linearly Transformed Role Functioning Scale Score).

"Time to Deterioration in Global Health Status and Quality of Life" or "GHS/QoL" refer to the time to the first documented 10 point decrease from a baseline measurement (e.g. by using the EORTC QLQ-C30 Linearly Transformed GHS/QoL Scale Score).

"Overall survival" or "OS" refers to the time from enrollment to death from any cause.

"Objective response rate" or "ORR" refers the percentage of patients with a confirmed complete response or partial response on two consecutive occasions ≥4 weeks apart, as determined by the investigator according to RECIST v1.1

"Time to progression" or "TTP" refers to the time from randomization until objective tumor progression.

"Duration of response" or "DOR" refers to the time from the first occurrence of a documented objective response to disease progression, as determined by the investigator according to RECIST v1.1, or death from any cause, whichever occurs first.

"Progression free survival" or "PFS" refers to the time from enrollment to the date of the first recorded occurrence of disease progression, as determined by the investigator using RECIST v1.1 or death from any cause, whichever occurs first.

"Clinical benefit rate" or "CBR" refers to the percentage of patients with stable disease for at least 24 weeks or with confirmed complete or partial response, as determined by the investigator according to RECIST v1.1.

"Complete response" or "CR" refers to the disappearance of all target lesions and non-target lesions and (if applicable) normalization of tumor marker level.

"Partial response" or "non-CR/Non-PD" refers to persistence of one or more non-target lesions and/or (if applicable) maintenance of tumor marker level above the normal limits. A PR can also refer to ≥30% decrease in sum of diameters of target lesions, in the absence of CR, new lesions, and unequivocal progression in non-target lesions.

"Progressive disease" or "PD" refers to ≥20% increase in sum of diameters of target lesions, unequivocal progression in non-target lesions, and/or appearance of new lesions.

"Stable disease" or "SD" refers to neither sufficient shrinkage to qualify for CR or PR nor sufficient increase growth of tumor to qualify for PD.

The term "locally advanced breast cancer" refers to cancer that has spread from where it started in the breast to nearby tissue or lymph nodes, but not to other parts of the body.

The term "metastatic breast cancer" refers to cancer that has spread from the breast to other parts of the body, such as the bones, liver, lungs, or brain. Metastatic breast cancer may also be referred to as stage IV breast cancer.

The term "treatment" refers to clinical intervention designed to alter the natural course of the patient or cell being treated during the course of clinical pathology. Desirable effects of treatment include decreasing the rate of disease progression, ameliorating or palliating the disease state, and remission or improved prognosis. For example, a patient is successfully "treated" if one or more symptoms associated with a breast cancer described herein are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of patients.

The term "delaying progression" of a disease refers to deferring, hindering, slowing, retarding, stabilizing, and/or postponing development of a breast cancer described herein. This delay can be of varying lengths of time, depending on the history of the cancer and/or patient being treated. As is evident to one skilled in the art, a sufficient or significant delay can, in effect, encompass prevention, in that the patient does not develop cancer.

An "effective amount" is at least the minimum amount required to effect a measurable improvement or prevention of a breast cancer described herein. An effective amount herein may vary according to factors such as the disease state, age, sex, and weight of the patient, and the ability of the agent to elicit a desired response in the patient. An effective amount is also one in which any toxic or detrimental effects of the treatment are outweighed by the therapeutically beneficial effects. Beneficial or desired results include results such as eliminating or reducing the risk, lessening the severity, delaying the onset of the disease (including biochemical, histological and/or behavioral symptoms of the disease, its complications and intermediate pathological phenotypes presenting during development of the disease), decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In some embodiments, an effective amount of the drug may have the effect in reducing the number of cancer cells; reducing the tumor size; inhibiting (i.e., slow or stop) cancer cell infiltration into peripheral organs; inhibit (i.e., slow or stop) tumor metastasis; inhibiting (i.e., slow or stop) tumor growth; and/or relieving one or more of the symptoms associated with the disorder. An effective amount can be administered in one or more administrations. An effective amount of drug, compound, pharmaceutical composition, or combination therapy described herein can be an amount sufficient to accomplish therapeutic treatment either directly or indirectly. As is understood in the clinical context, an effective amount of a drug, compound, or pharmaceutical composition may or may not be achieved in conjunction with another drug, compound, or pharmaceutical composition, or combination therapy. Thus, an "effective amount" may be considered in the context of administering one or more therapeutic agents, and a single agent may be considered to be given in an effective amount if, in conjunction with one or more other agents, a desirable result may be or is achieved.

An "E2-repressed score" as used herein, refers to a numerical value that reflects an aggregated expression level of a predetermined set of genes whose repression is reflective of estrogen receptor (ER) pathway activity.

An "E2-induced score" as used herein, refers to a numerical value that reflects an aggregated expression level of a predetermined set of genes whose induction is reflective of estrogen receptor (ER) pathway activity.

An "ER pathway activity score" as used herein, refers to a numerical value that reflects mathematical difference between the E2-induced score and the E2-repressed score.

An "administration period" or "cycle" refers to a period of time comprising administration of one or more agents described herein (i.e. GDC-9545 or a pharmaceutically acceptable salt thereof or palbociclib) and an optional period of time comprising no administration of one or more of the agents described herein. For example, a cycle can be 28 days in total length and include administration of one or more agents for 21 days and a rest period of 7 days. A "rest period" refers to a period of time where at least one of the agents described herein (e.g. GDC-9545 or a pharmaceutically acceptable salt thereof or palbociclib) are not administered. In one embodiment, a rest period refers to a period of time where none of the agents described herein (e.g. GDC-9545 or a pharmaceutically acceptable salt thereof or palbociclib) are administered. A rest period as provided herein can in some instances include administration of another agent that is not GDC-9545 or a pharmaceutically acceptable salt thereof or palbociclib. In such instances, administration of another agent during a rest period should not interfere or detriment administration of an agent described herein.

A "dosing regimen" refers to a period of administration of the agents described herein comprising one or more cycles, where each cycle can include administration of the agents described herein at different times or in different amounts.

"QD" refers to administration of a compound once daily.

"PO" refers to oral administration of an agent described herein.

A graded adverse event refers to the severity grading scale as established for by NCI CTCAE. In one embodiment, the adverse event is graded in accordance with the table below.

| Grade | Severity |
| --- | --- |
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living [a] |
| 3 | Severe or medically significant, but not immediately life-threatening; hospitalization or prolongation of hospitalization indicated; disabling; or limiting self-care activities of daily living [b, c] |
| 4 | Life-threatening consequences or urgent intervention indicated [d] |
| 5 | Death related to adverse event [d] |

Combination Therapies

Provided herein are combination therapies comprising GDC-9545 or a pharmaceutically acceptable salt thereof (e.g. GDC-9545·tartrate) and a CDK4/6 inhibitor. In one embodiment, the combination therapies are useful in the treatment of certain types of breast cancer as described herein. For example, in one embodiment, the combination therapies described herein can be used for treating estrogen receptor-postitive (ER+), human epidermal growth factor receptor 2-negative (HER2−) breast cancer. In another embodiment, the combination therapies described herein can be used for treating ER+, HER2− locally advanced breast cancer (laBC) or ER+, HER2− metastatic breast cancer (mBC). In one such embodiment, the combination therapies described herein can be used for treating ER+, HER2− laBC. In one such embodiment, the combination therapies described herein can be used for treating ER+, HER2− mBC.

In another aspect provided herein is a combination therapy comprising GDC-9545 or a pharmaceutically acceptable salt thereof (e.g. GDC-9545·tartrate) and palbociclib. As used herein, "palbociclib" refers to free base and any pharmaceutically acceptable salt of palbociclib.

The combination therapies described herein can be provided as a kit comprising one or more of the agents for administration. In one embodiment, the kit includes GDC-9545 or a pharmaceutically acceptable salt thereof for administration in combination with palbociclib as described herein. In another embodiment, the kit includes GDC-9545 or a pharmaceutically acceptable salt thereof packaged together with palbociclib, where the kit comprises separate formulated dosages of each agent. In still another embodiment, the kit includes GDC-9545 or a pharmaceutically acceptable salt thereof co-formulated with palbociclib.

Methods of Treating

Provided herein are methods of treating ER+, HER2− laBC or mBC in a patient having such a cancer. In one embodiment, the methods include treating ER+, HER2− laBC or mBC in a patient having such a cancer by administering to the patient a combination therapy as described herein over a 28-day cycle.

Further provided herein is a method of treating ER+, HER2− laBC or mBC in a patient having such a cancer where the method comprises administering to the patient a combination therapy comprising GDC-9545 or a pharmaceutically acceptable salt thereof and palbociclib, wherein said combination therapy is administered over one or more 28-day cycles.

Still further provided herein is a method of treating ER+, HER2− laBC or mBC in a patient having such a cancer where the method comprises administering to the patient a combination therapy described herein comprising a dosing regimen comprising: (i) administering GDC-9545 or a pharmaceutically acceptable salt thereof QD on days 1-28 of a first 28-day cycle; and (ii) administering palbociclib QD on days 1-21 of the first 28-day cycle.

In one embodiment, GDC-9545 or a pharmaceutically acceptable salt thereof is administered as a fixed dose or QD administration. In one embodiment, the administration is oral (PO), where GDC-9545 or a pharmaceutically acceptable salt thereof is formulated as a tablet or capsule. In one embodiment, GDC-9545 or a pharmaceutically acceptable salt thereof is administered at an amount of about 1 mg-100 mg, 1 mg-50 mg, 1 mg-30 mg, 10 mg-100 mg, 10 mg-50 mg, or 10 mg-30 mg QD. In another embodiment, GDC-9545 or a pharmaceutically acceptable salt thereof is adminsitered at an amount of about 1, 5, 10, 15, 20, 25, 30, 50, or 100 mg. In still another embodiment, GDC-9545 or a pharmaceutically acceptable salt thereof is administered at an amount of about 10, 30, 50, or 100 mg. In still another embodiment, GDC-9545 or a pharmaceutically acceptable salt thereof is administered at an amount of about 30 mg.

In one embodiment, palbociclib is administered according to a package insert. In a preferred embodiment, palbociclib is administed at an amount of 125 mg.

Still further provided herein is a method of treating ER+, HER2− laBC or mBC in a patient having such a cancer where the method comprises administering to the patient a combination therapy described herein comprising a dosing regimen comprising: (i) administering 30 mg GDC-9545 or a pharmaceutically acceptable salt thereof QD on days 1-28 of a first 28-day cycle; and (ii) administering 125 mg palbociclib QD on days 1-21 of the first 28-day cycle. In one such embodiment, the dosing regimen includes 2 or more cycles as described herein.

The methods of treating breast cancer as provided herein can include adminsitration of a combination therapy described herein as part of a dosing regimen. In one embodiment, the dosing regimen comprises one or more cycles. In another embodiment, the dosing regimen comprises at least 2 cycles. In another aspect provided herein is the dosing regimen comprises 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 cycles. In still another embodiment, dosing regimen comprises about 2-72, 2-66, 2-60, 2-54, 2-48, 2-42, 2-36, 2-30, 2-24, 2-18, or 2-12 cycles. In one embodiment, the dosing regimen includes administration of a combination therapy as described herein in any number of cycles until the desired response (e.g. PFS, OS, ORR, DOR, CBR) reaches a desired outcome (e.g. increase in PFS, OS, ORR, DOR, CBR compared to a control described herein). In another embodiment, the dosing regimen includes administration of a combination therapy as described herein in any number of cycles until toxicity develops or the patient otherwise experiences one or more adverse events (AEs) that prevents further administration. In still another embodiment, the dosing regimen includes administration of a combination therapy as described herein in any number of cycles until disease progression.

In one embodiment, the patient is a postmenopausal woman. In one such embodiment, the patient is (i) ≥60 years; (ii) Age <60 years and has ≥12 months of amenorrhea plus follicle-stimulating hormone (FSH) and plasma estradiol levels within postmenopausal range by local laboratory assessment, in the absence of oral contraceptive pills, hormone replacement therapy, or gonadotropin-releasing hormone agonist or antagonist; or (iii) has had documented bilateral oophorectomy.

In another embodiment, the patient is a premenopausal or perimenopausal (i.e., not postmenopausal) woman. In one such embodiment, the patient is treated with LHRH agonist in combination with a combination therapy described herein. The LHRH agonist therapy may be initiated 28 days prior to Day 1 of Cycle 1. In one embodiment, the LHRH agonist is administered on Day 1 of each cycle.

In another embodiment, the patient is a man. In one such embodiment, the patient is treated with a LHRH agonist in combination with a combination therapy described herein.

In one embodiment, a patient described herein has been tested for the presence of estrogen receptor, prostaglandin receptor, or Ki67. In one embodiment, a patient described herein has a documented ER-positive tumor according to American Society of Clinical Oncology/College of American Pathologists guidelines. In one such embodiment, a patient described herein has a documented HER2-negative tumor. In one embodiment, a patient described herein has had prior treatment with an aromatase inhibitor (e.g. anastrozole, exemestane, or letrozole) or a CDK4/6 inhibitor (e.g. palbociclib), or a combination thereof. In one such embodiment, the patient did not have disease recurrence during or within 12 months of completing such treatment with an aromatase inhibitor or CDK4/6 inhibitor).

In one embodiment, a patient described herein is treatment naive. In another embodiment, a patient described herein has not received prior chemotherapy before administration of the combination therapy. In another embodiment, a patient described herein has not been previously treated with an aromatase inhibitor or a CDK4/6 inhibitor or a combination thereof. In one such embodiment, the CDK4/6 inhibitor is palbociclib. In another such embodiment, the aromatase inhibitor is anastrozole, exemestane, or letrozole. In one embodiment, a patient described herein has not been previously treated with either letrozole or palbociclib. In still another embodiment, a patient described herein has not received surgery, chemotherapy, or radiotherapy at least 14 days before administration of the combination therapy described herein. In still another embodiment, a patient described herein has not been previously treated with a SERD (e.g. fulvestrant) or with tamoxifen. In another embodiment, a patient may have been previously treated with tamoxifen, provided that the patient did not exhibit disease recurrence within the first 24 months of treatment with tamoxifen.

In one embodiment of the methods described herein, a patient has been treated with one or more cancer therapies before administration of a combination therapy described herein. In one embodiment of the methods described herein, a patient has breast cancer described herein that is resistant to one or more cancer therapies. In one embodiment of the methods described herein, resistance to cancer therapy includes recurrence of cancer or refractory cancer. Recurrence may refer to the reappearance of cancer, in the original site or a new site, after treatment. In one embodiment of the methods described herein, resistance to a cancer therapy includes progression of the cancer during treatment with the anti-cancer therapy. In some embodiments of the methods described herein, resistance to a cancer therapy includes cancer that does not response to treatment. The cancer may be resistant at the beginning of treatment or it may become resistant during treatment. In some embodiments of the methods described herein, the cancer is at early stage or at late stage.

Systemic chemotherapy is considered as one standard of care (SOC) for patients with mBC, although no standard regimen or sequence exists. In one embodiment of the methods described herein, a patient described herein has been previously treated with one or more of the therapies selected from the group consisting of anastrozole, letrozole, exemestane, everolimus, palbociclib and letrozole, fulvestrant, tamoxifen, toremifene, megestrol acetate, fluoxemesterone, ethinyl estradiol doxorubicin, pegylated liposomal doxorubicin, epirubicin, cyclophosphamide, docetaxel, paclitaxel, albumin-bound paclitaxel, methotrexate, 5-fluorouracil (5-FU), methotrexate and 5-fluorouracil (5-FU), carboplatin, cisplatin, capecitabine, gemcitabine, vinorelbine, eribulin, ixabepilone, trastuzumab and pertuzumab, or a combination thereof prior to administration of a combination therapy described herein.

In one embodiment of the methods described herein, a patient described herein can have IaBC or mBC as described herein that is resistant to one or more of the single agent therapies selected from the group consisting of anastrozole, letrozole, exemestane, everolimus, palbociclib and letrozole, fulvestrant, tamoxifen, toremifene, megestrol acetate, fluoxemesterone, ethinyl estradiol doxorubicin, pegylated liposomal doxorubicin, epirubicin, cyclophosphamide, docetaxel, paclitaxel, albumin-bound paclitaxel, methotrexate, 5-fluorouracil (5-FU), methotrexate and 5-fluorouracil (5-FU), carboplatin, cisplatin, capecitabine, gemcitabine, vinorelbine, eribulin, ixabepilone, trastuzumab and pertuzumab, or a combination thereof.

In one embodiment of the methods described herein, a patient described herein may have undergone surgical treatment such as, for example, surgery that is breast-conserving (i.e., a lumpectomy, which focuses on removing the primary tumor with a margin), or more extensive (i.e., mastectomy, which aims for complete removal of all of the breast tissue) prior to administration of a combination therapy described herein. In another embodiment, a patient described herein may undergo surgical treatment following treatment with a combination therapy described herein.

Radiation therapy is also administered post-surgery to the breast/chest wall and/or regional lymph nodes, with the goal of killing microscopic cancer cells left post-surgery. In the case of a breast conserving surgery, radiation is administered to the remaining breast tissue and sometimes to the regional lymph nodes (including axillary lymph nodes). In the case of a mastectomy, radiation may still be administered if factors that predict higher risk of local recurrence are present. In some embodiments of the methods provided herein a patient described herein may have received radiation therapy prior to administration of a combination therapy described herein. In other embodiments of the methods provided herein a patient described herein may have receive radiation therapy following administration of a combination therapy described herein.

In some embodiments, a patient described herein does not have a history of other malignancy within 5 years prior to administration of a combination therapy described herein. In some embodiments, a patient described herein does not have active inflammatory bowel disease, chronic diarrhea, short bowel syndrome, or major upper gastrointestinal surgery including gastric resection. In some embodiments, a patient described herein does not have cardiac disease or cardiac dysfunction.

In one embodiment, treatment with a combination therapy according to the methods provided herein increases a patient's OS comparable to a control (e.g. non-treatment, standard of care (SOC) treatment, or a combination of palbociclib and letrozole). In one embodiment, treatment with a combination therapy according to the methods provided herein increases a patient's OS comparable to a control (e.g. non-treatment, standard of care (SOC) treatment, or a combination of palbociclib and letrozole) by 1, 2, 3, 4, 5, 6, 7, 8, 9, 10, 11, 12, 14, 16, 18, 20, 24 or more months comparable to the control.

In one embodiment, treatment with a combination therapy according to the methods provided herein increases the patient's amount of ORR. In one such embodiment, treatment with a combination therapy according to the methods provided herein results in more patients having a complete response (CR) or partial response (PR) than a control. In another embodiment, the TTP is increased in a patient following treatment with a combination therapy according to the methods provided herein. In still another embodiment, duration of response to the combination therapy is increased compared to a control (e.g. non-treatment, standard of care (SOC) treatment, or a combination of palbociclib and letrozole). In one such embodiment, the duration of response is increased by at least 1-3, 2-6, 3-8, 4-10, 5-12, 6-15, 8-20, or 1-24 months. In still another embodiment, a patient described herein has increased clinical benefit rate compared to a control (e.g. non-treatment, standard of care (SOC) treatment, or a combination of palbociclib and letrozole). In still another embodiment, a patient has increased progression-free survival compared to a control (e.g. non-treatment, standard of care (SOC) treatment, or a combination of palbociclib and letrozole).

In one embodiment provided herein a patient is diagnosed having a CR following treatment with a combination therapy according to the methods provided herein. In one embodiment provided herein a patient is diagnosed having a PR following treatment with a combination therapy according to the methods provided herein. In one embodiment provided herein a patient is diagnosed having SD following treatment with a combination therapy according to the methods provided herein.

Further provided herein is the use of a combination therapy described herein comprising GDC-9545 or a pharmaceutically acceptable salt thereof and palbociclib as described herein for the treatment of laBC or mBC as described herein.

Further provided herein is the use of a combination therapy described herein comprising GDC-9545 or a pharmaceutically acceptable salt thereof and palbociclib as described herein for the treatment of mBC as described herein. Still further provided herein is the use of a combination therapy described herein comprising GDC-9545 or a pharmaceutically acceptable salt thereof and palbociclib as described herein for the treatment of laBC as described herein.

Further provided herein is the use of a combination therapy described herein comprising GDC-9545 or a pharmaceutically acceptable salt thereof and palbociclib as described herein for the manufacture of a medicament for the treatment of laBC or mBC as described herein. Still further provided herein is the use of a combination therapy described herein comprising GDC-9545 or a pharmaceutically acceptable salt thereof and palbociclib as described herein for the manufacture of a medicament for the treatment of mBC as described herein. Further provided herein is the use of a combination therapy described herein comprising GDC-9545 or a pharmaceutically acceptable salt thereof and palbociclib described herein for the manufacture of a medicament for the treatment of laBC as described herein.

Also provided herein are methods of inhibiting tumor growth or producing tumor regression in a patient described herein by administering a combination therapy described herein. In one embodiment provided herein is a method of inhibiting tumor growth in a patient having laBC described herein by administering a combination therapy comprising administering GDC-9545 or a pharmaceutically acceptable salt thereof and palbociclib in one or more 28-day cycles as described herein. In one embodiment provided herein is a method of inhibiting tumor growth in a patient having mBC described herein by administering a combination therapy comprising administering GDC-9545 or a pharmaceutically acceptable salt thereof and palbociclib in one or more 28-day cycles as described herein.

In one embodiment provided herein is a method of producing or improving tumor regression in a patient having mBC described herein by administering a combination therapy comprising administering GDC-9545 or a pharmaceutically acceptable salt thereof and palbociclib in one or more 28-day cycles as described herein. In one embodiment provided herein is a method of producing or improving tumor regression in a patient having laBC described herein by administering a combination therapy comprising administering GDC-9545 or a pharmaceutically acceptable salt thereof and palbociclib in one or more 28-day cycles as described herein.

The development of combination treatments poses challenges including, for example, the selection of agents for combination therapy that may lead to improved efficacy while maintaining acceptable toxicity. One particular challenge is the need to distinguish the incremental toxicity of the combination. In one embodiment of the methods described herein the combination therapy described herein (e.g. GDC-9545 or a pharmaceutically acceptable salt thereof and palbociclib) is administered in a dosing regimen comprising a staggered dosing schedule. In one such embodiment, the patient has a reduced number or grade of adverse events (AEs) comparable to a control (e.g. SOC therapy or palbociclib and letrozole).

In one embodiment of the methods described herein, the dosing regimen reduces the number or frequency of grade 2 or grade 3 or higher grade adverse event comparable to administration of palbociclib and letrozole. In one such embodiment, the dosing regimen eliminates the number or frequency of grade 3 or higher AEs.

In another embodiment of the methods described herein the dosing reduces the number or frequency of grade 2 or grade 3 or higher grade adverse event comparable to administration of either agent alone.

It is generally understood that the when an adverse event occurs, four options exist: (1) continue treatment as-is with optional concomitant therapy; (2) adjust the dose of one or more agents in the dosing regiment; (3) suspend administration of one or more agents in the dosing regimen; or (4) discontinue administration of one or more agents in the dosing regimen.

In one embodiment of the methods described herein, a patient described herein experiences one or more adverse events comprising fatigue, cough, pain, arthralgia, neutropenia, bradycardia, diarrhea, constipation, dizziness, nausea, anemia, asthenia, thrombocytopenia, or pruritus. In one such embodiment, a patient described herein has the same level or reduced level/severity of one or more of such AEs. In another embodiment, a patient described herein has a reduced severity of one or more of such AEs. In one embodiment, a patient described herein has a reduced severity of neutropenia, diarrhea, or bradycardia compared to a control. In one such embodiment, the control is (i) either agent along; (ii) palbociclib and letrozole; or (iii) SOC therapy.

In one embodiment, a patient described herein has the same level or reduced level of neutropenia following administration of the combination therapy compared to the control. In one such embodiment, the control is palbociclib alone; GDC-9545 or a pharmaceutically acceptable salt thereof alone; palbociclib and letrozole; or SOC therapy. In another embodiment, the control is palbociclib alone or palbociclib and letrozole. In still another embodiment, a patient described herein has the same level or reduced level of bradycardia following administration of the combination therapy compared to the control. In another embodiment, the control is GDC-9545 or a pharmaceutically acceptable salt thereof alone or palbociclib and letrozole.

In one embodiment, the adverse event(s) experienced by a patient described herein undergoing treatment with a combination therapy described herein are comparably reduced as described herein.

In one embodiment of the methods described herein, a patient described herein experiences an adverse event comprising diarrhea. In one embodiment of the methods described herein, less than 75%, 60%, 50%, 40%, 33%, 25%, 20% 12% or 5% A of all patients treated experience one or more of neutropenia, diarrhea, or bradycardia from treatment with a combination therapy described herein. In one embodiment of the methods described herein, less than 85%, 75%, 60%, 50%, 40%, 33%, 25%, 20% 17%, 10% or 5% of all patients treated experience a diarrhea as described herein from treatment with a combination therapy described herein. In one embodiment of the methods described herein, less than 60%, 50%, 45%, 33%, 25%, 10% or 5% A of all patients treated experience neutropenia from treatment with a combination therapy described herein. In one embodiment of the methods described herein, less than 75%, 60%, 50%, 40%, 33%, 25%, 20% 15%, 10% or 8% A of all patients treated experience bradycardia as described herein from treatment with a combination therapy described herein. In some embodiments, where a patient experiences one or more AEs selected from the group consisting of neutropenia, diarrhea, and bradycardia from treatment with a combination therapy described herein, the severity is Grade 2 or less. In one embodiment, a patient described herein does not experience one or more AEs selected from the group consisting of neutropenia, diarrhea, and bradycardia from treatment with a combination therapy described herein, where the severity of the AE is higher than Grade 2.

Biomarkers

Breast cancer is a heterogeneous disease with many distinct subtypes as defined by molecular signatures and a diverse array of mutational profiles. Patients described herein can be tested for ER+ HER2– laBC or mBC using diagnostic methods, or kits to inform treating or predict of responsiveness of a pateint to the combination therapies described herein. In one embodiment, a patient can be tested by determining an ER pathway activity score such as those described in US Patent Application Publication 20200082944. In some embodiments, a patient sample is taken and tested to determine an ER pathway activity score. The score can be calculated using a 41-gene signature by subtracting an E2-repressed score (as determined from the average z-scored expression of genes comprising BAMBI, BCAS1, CCNG2, DDIT4, EGLN3, FAM171B, GRM4, IL1R1, LIPH, NBEA, PNPLA7, PSCA, SEMA3E, SSPO, STON1, TGFB3, TP531NP1, and TP531NP2) from an E2-induced score (as determined from the average z-scored expression of genes set forth in AGR3, AMZ1, AREG, C5AR2, CELSR2, CT62, FKBP4, FMN1, GREB1, IGFBP4, NOSIAP, NXPH3, OLFM1, PGR, PPMIJ, RAPGEFLI, RBM24, RERG, RET, SGK3, SLC9A3R1, TFF1, and ZNF703).

In one embodiment, the sample from the patient used for determining the ER pathway activity score is a tumor tissue sample, (e.g., a formalin-fixed paraffin-embedded (FFPE), a fresh frozen (FF), an archival, a fresh, or a frozen tumor tissue sample).

In some instances, a patient described herein is administered a combination therapy described herein where the measured ER pathway activity score is be between about −1.0 to about −0.2 (e.g., between about −0.9 to about −0.2, e.g., between about −0.8 to about −0.2, e.g., between about −0.7 to about −0.2, e.g., between about −0.6 to about −0.2, e.g., between about −0.5 to about −0.2, e.g., between about −0.4 to about −0.2, or e.g., between about −0.3 to about −0.2). In some instances, the ER activity score from the sample may be less than −1.0.

In some embodiments, samples of patients described herein can be assessed for additional biomarkers in an effort to identify factors that may correlate with the safety and efficacy of the study treatments.

In one embodiment of the methods described herein, NGS, whole genome sequencing (WGS), other methods, or a combination thereof can be used for DNA obtained from blood samples and tumor tissue from patients described herein. Such samples may be analyzed to identify germline (e.g., BRCA1/2) and somatic alterations that are predictive of response to study drug, are associated with progression to a more severe disease state, are associated with acquired resistance to study drug, or can increase the knowledge and understanding of disease biology.

EMBODIMENTS

Provided below are exemplary embodiments of the invention.

Embodiment No 1. A method of treating estrogen receptor-positive and HER2– negative locally advanced breast cancer (laBC) or metastatic breast cancer (mBC) in a patient having receptor-positive and HER2-negative laBC or mBC, the method comprising administering to the patient a combination therapy comprising GDC-9545 or a pharmaceutically acceptable salt thereof and a CDK4/6 inhibitor, wherein said combination therapy is administered over a 28-day cycle.

Embodiment No 2. A method of treating estrogen receptor-positive and HER2– negative locally advanced breast cancer (laBC) or metastatic breast cancer (mBC) in a patient having receptor-positive and HER2-negative laBC or mBC, the method comprising administering to the patient a combination therapy comprising GDC-9545 or a pharmaceutically acceptable salt thereof and palbociclib, wherein said combination therapy is administered over one or more 28-day cycles.

Embodiment No 3. A method of treating estrogen receptor-positive and HER2– negative locally advanced breast cancer (laBC) or metastatic breast cancer (mBC) in a patient having receptor-positive and HER2-negative laBC or mBC, the method comprising administering to the patient a combination therapy comprising a dosing regimen comprising:
  (i) administering GDC-9545 or a pharmaceutically acceptable salt thereof QD on days 1-28 of a first 28-day cycle; and
  (ii) administering palbociclib QD on days 1-21 of the first 28-day cycle.

Embodiment No 4. The method of embodiment 1, wherein the CDK4/6 inhibitor is palbociclib.

Embodiment No 5. The method of any one of embodiments 1-4, wherein GDC-9545 or a pharmaceutically acceptable salt thereof is administered at an amount of about 10 mg to about 100 mg.

Embodiment No 6. The method of embodiment 5, wherein GDC-9545 or a pharmaceutically acceptable salt thereof is administered at an amount of about 10, 30, 50, or 100 mg.

Embodiment No 7. The method of embodiment 5, wherein GDC-9545 or a pharmaceutically acceptable salt thereof is administered at an amount of about 30 mg.

Embodiment No 8. The method of any one of embodiments 2-7, wherein palbociclib is administered at an amount of about 125 mg.

Embodiment No 9. The method of any one of embodiments 3-8, wherein the dosing regimen comprises 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 cycles.

Embodiment No 10. The method of any one of embodiments 3-8, wherein the dosing regimen comprises about 2-72, 2-66, 2-60, 2-54, 2-48, 2-42, 2-36, 2-30, 2-24, 2-18, or 2-12 cycles.

Embodiment No 11. The method of any one of embodiments 1-8, wherein the patient is premenopausal.

Embodiment No 12. The method of any one of embodiments 1-8, wherein the patient is male.

Embodiment No 13. The method of embodiment 11 or 12, wherein the patient is further administered luteinizing hormone-releasing hormone (LHRH).

Embodiment No 14. The method of embodiment 13, wherein the patient is administered LHRH on day one of each cycle.

Embodiment No 15. The method of any one of embodiments 1-14, wherein the patient is tested for the presence of a mutation of one or more of estrogen receptor, prostaglandin receptor, or Ki67.

Embodiment No 16. The method of any one of embodiments 1-15, wherein the patient reduced adverse events (AEs) comparable to a control.

Embodiment No 17. The method of embodiment 16, wherein the control is letrozole administered in combination with palbociclib.

Embodiment No 18. The method of any one of embodiments 16-17, wherein the number or frequency of grade 3 or higher AEs is reduced.

Embodiment No 19. The method of any one of embodiments 16-18, wherein the patient has reduced severity of one or more AEs selected from the group consisting of fatigue, cough, pain, arthralgia, neutropenia, bradycardia, diarrhea, constipation, dizziness, nausea, anemia, asthenia, thrombocytopenia, or pruritus compared to the control.

Embodiment No 20. The method of any one of embodiments 1-19, wherein the patient has the same level or reduced level of neutropenia following administration of the combination therapy compared to the control.

Embodiment No 21. The method of any one of embodiments 1-20, wherein the patient has the same level or reduced level of bradycardia following administration of the combination therapy compared to the control.

Embodiment No 22. The method of any one of embodiments 1-21, wherein the patient has an increased overall survival (OS) comparable to a control.

Embodiment No 23. The method of embodiment 22, wherein the patient has an increase of 1, 2, 3, 4, 5, 6, 7, 8, 9, 10, 11, 12, 14, 16, 18, 20, 24 or more months comparable to a control.

Embodiment No 24. The method of any one of embodiments 1-23, wherein the objective response rate of the patient to the combination therapy results in more patients having a complete response (CR) or partial response (PR) than a control.

Embodiment No 25. The method of any one of embodiments 1-24, wherein duration of response to the combination therapy is increased compared to a control.

Embodiment No 26. The method of embodiment 25, wherein the duration of response is increased by at least 1-3, 2-6, 3-8, 4-10, 5-12, 6-15, 8-20, or 1-24 months.

Embodiment No 27. The method of any one of embodiments 1-26, wherein a patient has increased clinical benefit rate compared to a control.

Embodiment No 28. The method of any one of embodiments 1-27, wherein a patient has increased progression-free survival compared to a control.

Embodiment No 29. The method of embodiment 28, wherein the increase is at least 2, 4, 6, 8, 10, 12, 14, 16, 18, 20, 22, 24, 26, 28, 30, 36, 42, 48, 50, 54, 60, 66, or 72 months.

Embodiment No 30. The method of any one of embodiments 1-29, wherein the patient has a decreased time to deterioration in (i) pain level; (ii) pain presence and interference; (iii) physical functioning; (iv) role functioning; (v) global health status and quality of life; or (vi) a combination thereof.

Embodiment No 31. The method any one of embodiments 22-30, wherein the control is palbociclib alone or palbociclib administered in combination with letrozole.

Embodiment No 32. The method of any one of embodiments 1-31, wherein the patient is postmenopausal.

Embodiment No 33. The method of embodiment 32, wherein the patient has had bilateral oophorectomy.

Embodiment No 34. The method of any one of embodiments 1-33, wherein the patient has not received prior chemotherapy before administration of the combination therapy.

Embodiment No 35. The method of any one of embodiments 1-33, wherein the patient has been previously treated with tamoxifen.

Embodiment No 36. The method of any one of embodiments 1-33, wherein the patient has been previously treated with an aromatase inhibitor or a CDK4/6 inhibitor or a combination thereof.

Embodiment No 37. The method of any one of embodiments 1-33, wherein the patient has not been previously treated with an aromatase inhibitor or a CDK4/6 inhibitor or a combination thereof.

Embodiment No 38. The method of any one of embodiments 1-33, wherein the patient has not received surgery, chemotherapy, or radiotherapy at least 14 days before administration of the combination therapy.

Embodiment No 39. The method of any one of embodiments 1-33, wherein the patient does not have cardiac disease or cardiac dysfunction.

Embodiment No 40. Use of a combination therapy comprising GDC-9545 or a pharmaceutically acceptable salt thereof and palbociclib for the treatment of laBC or mBC as described herein.

Embodiment No 41. Use of a combination therapy comprising GDC-9545 or a pharmaceutically acceptable salt thereof and palbociclib for the manufacture of a medicament for the treatment of laBC or mBC.

Embodiment No 42. A method of inhibiting tumor growth in a patient having laBC or mBC, the method comprising administering a combination therapy comprising GDC-9545 or a pharmaceutically acceptable salt thereof and palbociclib in one or more 28-day cycles.

Embodiment No 43. A method of producing or improving tumor regression in a patient having laBC or mBC, the method comprising administering a combination therapy comprising GDC-9545 or a pharmaceutically acceptable salt thereof and palbociclib in one or more 28-day cycles.

The following Examples are presented by way of illustration, not limitation.

EXAMPLES

Patients: Eligible patients had ER+ (HER2−) metastatic breast cancer with ≤2 prior therapies in the advanced or metastatic setting that had recurred or progressed while being treated with adjuvant endocrine therapy for a duration of ≥24 months and/or endocrine therapy in the incurable, locally advanced, or metastatic setting and derived a clinical benefit from therapy (i.e., tumor response or stable disease for at least 6 months). No prior treatment with CDK4/6i was allowed in patients receiving palbociclib.

TABLE 1

Patient demographics and disease characterization.

| Characteristic | Cohort A GDC-9545 100 mg (n = 40) | Cohort B GDC-9545 100 mg + palbociclib 125 mg (n = 48) | All Patients (n = 88) |
|---|---|---|---|
| Median age | 56 (33-76) | 57 (33-80) | 56 (33-80) |
| ECOG status at baseline | | | |
| 0 | 27 (68%) | 30 (63%) | 57 (65%) |
| 1 | 13 (33%) | 18 (38%) | 31 (35%) |
| Median prior regimens | | | |
| Median overall | 1 (1-2) | 1 (0-2) | 1 (0-2) |
| Prior CDK4/6i | 15 (38%) | 0 (0%) | 15 (17%) |
| Prior Fulvestrant | 7 (18%) | 3 (7%) | 10 (11%) |
| ESR1 ctDNA baseline status | | | |
| Wildtype | 25 (63%) | 30 (63%) | 55 (63%) |
| Mutant | 13 (33%) | 14 (29%) | 27 (30%) |
| Unknown | 2 (1%) | 4 (8%) | 6 (7%) |
| Reason for discontinuation | | | |
| Disease progression | 22 (55%) | 11 (23%) | 33 (38%) |
| Physician decision | 1 (3%) | 1 (2%) | 2 (2%) |
| Death | 1 (3%) | 1 (2%) | 2 (2%) |
| Other | 1 (3%) | 0 (0%) | 1 (1%) |

Safety. Treatment-emergent AEs (TEAE) have been reported in 78% and 96% of patients treated in Cohorts A and B, respectively. In Cohort A, 58% of patients had an AE related to GDC-9545; these were generally Grade 1-2, except three Grade 3 events of fatigue, transaminase increased, and diarrhea. No patients discontinued study treatment due to AEs. In Cohort B, 58% of patients had an AE related to GDC-9545; AEs were Grade 1 or 2 severity, except one SAE of Grade 3 QT prolongation with T-wave inversion reported in a 69-year-old female. This patient had a baseline QTcF of 441 ms and on the Cycle 6 Day 1 visit her QTcF was 506 ms while asymptomatic. This case was confounded by the patient's medical history of pre-existing coronary artery disease (30-50% stenosis of coronary arteries), right bundle branch block, and possible use of pregabalin during the same time. Therapy with palbociclib and GDC-9545 was withdrawn in response to the QT prolongation, which resolved approximately 16 days after onset.

Bradycardia AEs were reported in three patients (8%) in Cohort A and 15 (31%) in Cohort B; all were Grade 1 and asymptomatic, except Grade 2 bradycardia in one patient (Cohort B) who also experienced Grade 2 dizziness. ECG data showed similar heart rate changes in Cohorts A and B with no further heart rate change with the addition of palbociclib. Heart rate (HR) changes returned to baseline upon completion of treatment. The mean maximum HR change in both cohorts was 19 and 20 beats per minute (bpm) for those with baseline HR≥60 bpm, and was 13 bpm in Cohorts A and B respectively, for those with baseline HR<60 bpm.

TABLE 2

All adverse events occuring in ≥10% of patients

| AE Name | Cohort A GDC-9545 100 mg (n = 40) | | Cohort B GDC-9545 100 mg + palbociclib 125 mg (n = 48) | | All Patients (n = 88) | |
|---|---|---|---|---|---|---|
|  | All Grades | Grade ≥3 | All Grades | Grade ≥3 | All Grades | Grade ≥3 |
| Neutropenia | 2 (5%) | 0 | 37 (77%) | 29 (60%) | 39 (44%) | 29 (33%) |
| Fatigue | 9 (23%) | 2 (5%) | 14 (29%) | 0 | 23 (26%) | 2 (2%) |
| Diarrhea | 4 (10%) | 1 (3%) | 16 (33%) | 1 (2%) | 20 (23%) | 2 (2%) |
| Bradycardia | 3 (8%) | 0 | 15 (31%) | 0 | 18 (21%) | 0 |
| Cough | 6 (15%) | 0 | 10 (21%) | 0 | 16 (18%) | 0 |
| Constipation | 4 (10%) | 0 | 10 (21%) | 0 | 14 (16%) | 0 |
| Nausea | 3 (8%) | 0 | 10 (21%) | 0 | 13 (15%) | 0 |
| Dizziness | 2 (5%) | 0 | 9 (19%) | 0 | 11 (13%) | 0 |
| Anemia | 1 (3%) | 0 | 8 (17%) | 0 | 9 (10%) | 0 |
| Throbocytopenia | 1 (3%) | 1 (3%) | 8 (17%) | 3 (6%) | 9 (10%) | 4 (5%) |

Pharmacokinetics. Exposure of GDC-9545 in combination with palbociclib was generally comparable to that observed with single agent GDC-9545. Palbociclib PK was not altered when given with GDC-9545 and was consistent with reported values.

Pharmacodynamic Effects. Reduced ER ($10/12$, 83%), PR ($7/8$, 88%), and Ki67 ($9/12$, 75%) protein levels, and ER pathway signature scores ($8/12$, 67%) (Guan et al, Cell, 2019) were observed in evaluable paired pre- and on-treatment biopsies (n=12).

Decreases from baseline in ctDNA ESR1 mutant allele frequency observed in all patients in both cohorts (n=26).

Clinical Activity. In Cohort A $22/40$ patients (55%) derived clinical benefit defined as patients with CR, PR or first occurrence of progressive disease observed on or after 24 weeks. Partial response was observed in $4/31$ (13%) of patients with measurable disease at baseline. In Cohort B $35/48$ (81%) patients had clinical benefit and $14/45$ (33%) had a PR. Across both cohorts, clinical benefit was observed in patients with prior fulvestrant treatment [$2/7$ (29%) and $2/3$ (67%) for Cohorts A and B respectively] and with detectable ESR1 mutations at enrollment [$8/13$ (62%) and $11/11$ (100%)].

TABLE 3

Efficacy results.

| Characteristic | Cohort A GDC-9545 100 mg (n = 40) | Cohort B GDC-9545 100 mg + palbociclib 125 mg (n = 48) |
|---|---|---|
| Patients with an event of disease progression or death for PFS calculations | 55% | 29% |
| Median PFS (months) | 7.8 | 9.3 |
| Clinical benefit | 40 | 43 |
| CBR | 55% | 81% |
| Patients with measurable disease | 31 | 45 |
| Patients with confirmed response | 4 | 15 |
| ORR | 13% | 33% |
| Patients with unconfirmed response | 4 | 18 |

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed herein. The upper and lower limits of these small ranges which can independently be included in the smaller rangers is also encompassed herein, subject to any specifically excluded limit in the stated range. Where the stated range includes one or both of the limits, ranges excluding either or both of those included limits are also included herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method of treating estrogen receptor-positive and HER2-negative locally advanced breast cancer (laBC) or metastatic breast cancer (mBC) in a patient having receptor-positive and HER2-negative laBC or mBC, the method comprising administering to the patient a combination therapy comprising GDC-9545 or a pharmaceutically acceptable salt thereof and palbociclib, wherein said combination therapy is administered over one or more 28-day cycles.

2. The method of claim 1, wherein the method further comprises administering to the patient a dosing regimen comprising:
   (i) administering GDC-9545 or a pharmaceutically acceptable salt thereof QD on days 1-28 of a first 28-day cycle; and
   (ii) administering palbociclib QD on days 1-21 of the first 28-day cycle.

3. The method of claim 1, wherein GDC-9545 or a pharmaceutically acceptable salt thereof is administered at an amount of about 10 mg to about 100 mg.

4. The method of claim 3, wherein GDC-9545 or a pharmaceutically acceptable salt thereof is administered at an amount of about 10, 30, 50, or 100 mg.

5. The method of claim 3, wherein GDC-9545 or a pharmaceutically acceptable salt thereof is administered at an amount of about 30 mg.

6. The method of claim 1, wherein palbociclib is administered at an amount of about 125 mg.

7. The method of claim 2, wherein the dosing regimen comprises 2, 3, 4, 5, 6, 7, 8, 9, 10, 11, 12, 13, 14, 15, 16, 17, 18, 19, 20, 21, 22, 23, 24, 30, 36, 42, 48, 54, 60, 66, or 72 cycles.

8. The method of claim 2, wherein the dosing regimen comprises about 2-72, 2-66, 2-60, 2-54, 2-48, 2-42, 2-36, 2-30, 2-24, 2-18, or 2-12 cycles.

9. The method of claim 1, wherein the patient is premenopausal.

10. The method of claim 1, wherein the patient is male.

11. The method of claim 9, wherein the patient is further administered luteinizing hormone-releasing hormone (LHRH).

12. The method of claim 11, wherein the patient is administered LHRH on day one of each cycle.

13. The method of claim 1, wherein the patient is tested for the presence of a mutation of one or more of estrogen receptor, prostaglandin receptor, or Ki67.

14. The method of claim 1, wherein the patient has a reduced number of freqency of grade 3 adverse events (AEs) comparable to a control.

15. The method of claim 14, wherein the patient has reduced severity of one or more AEs selected from the group consisting of fatigue, cough, pain, arthralgia, neutropenia, bradycardia, diarrhea, constipation, dizziness, nausea, anemia, asthenia, thrombocytopenia, or pruritus compared to the control.

16. The method of claim 1, wherein the patient has a decreased time to deterioration in (i) pain level; (ii) pain presence and interference; (iii) physical functioning; (iv) role functioning; (v) global health status and quality of life; or (vi) a combination thereof.

17. The method claim 14, wherein the control is palbociclib administered in combination with letrozole.

18. The method of claim 1, wherein the patient is postmenopausal.

19. The method of claim 18, wherein the patient has had bilateral oophorectomy.

20. The method of claim 1, wherein the patient has not received prior chemotherapy before administration of the combination therapy.

21. The method of claim 1, wherein the patient has been previously treated with tamoxifen.

22. The method of claim 1, wherein the patient has been previously treated with an aromatase inhibitor or a CDK4/6 inhibitor or a combination thereof.

23. The method of claim 1, wherein the patient has not been previously treated with an aromatase inhibitor or a CDK4/6 inhibitor or a combination thereof.

24. The method of claim 1, wherein the patient has not received surgery, chemotherapy, or radiotherapy at least 14 days before administration of the combination therapy.

25. The method of claim 1, wherein the patient does not have cardiac disease or cardiac dysfunction.

26. A method of inhibiting tumor growth in a patient having laBC or mBC, the method comprising administering a combination therapy comprising GDC-9545 or a pharmaceutically acceptable salt thereof and palbociclib in one or more 28-day cycles.

27. A method of producing or improving tumor regression in a patient having laBC or mBC, the method comprising administering a combination therapy comprising GDC-9545 or a pharmaceutically acceptable salt thereof and palbociclib in one or more 28-day cycles.

* * * * *